United States Patent
Xilinas et al.

(10) Patent No.: US 7,030,136 B2
(45) Date of Patent: *Apr. 18, 2006

(54) USE OF PHANQUINONE FOR THE TREATMENT OR PREVENTION OF MEMORY IMPAIRMENT

(75) Inventors: Michel Xilinas, Memeou (CY); Panayotis Nikolas Gerolymatos, Kryoneri Attika (GR)

(73) Assignee: Prana Biotechnology Limited, Parkville (AU)

( * ) Notice: Subject to any disclaimer, the term of this patent is extended or adjusted under 35 U.S.C. 154(b) by 151 days.

This patent is subject to a terminal disclaimer.

(21) Appl. No.: 10/098,922

(22) Filed: Mar. 15, 2002
(Under 37 CFR 1.47)

(65) Prior Publication Data

US 2003/0055078 A1    Mar. 20, 2003

Related U.S. Application Data

(63) Continuation of application No. 09/895,807, filed on Jun. 26, 2001, now abandoned, which is a continuation of application No. PCT/IB00/00011, filed on Jan. 6, 2000, now abandoned.

(30) Foreign Application Priority Data

Jan. 7, 1999    (GR)    ................................ 990100005

(51) Int. Cl.
*A61K 31/47*    (2006.01)

(52) U.S. Cl. ...................................... 514/307; 514/309

(58) Field of Classification Search ................ 514/307, 514/309
See application file for complete search history.

(56) References Cited

U.S. PATENT DOCUMENTS

| | | | | |
|---|---|---|---|---|
| 4,845,115 | A | * | 7/1989 | Tyers ........................ 514/397 |
| 5,091,391 | A | | 2/1992 | Aizenman et al. |
| 5,792,774 | A | * | 8/1998 | Haughan et al. ............ 514/294 |
| 5,866,597 | A | * | 2/1999 | Baxter ........................ 514/242 |
| 5,980,914 | A | | 11/1999 | Gerolymatos |
| 5,994,323 | A | | 11/1999 | Gerolymatos |
| 6,001,852 | A | | 12/1999 | Gerolymatos |
| 6,670,369 | B1 | * | 12/2003 | Xilinas et al. .............. 514/282 |

FOREIGN PATENT DOCUMENTS

| | | |
|---|---|---|
| EP | 613 560 | 9/1994 |
| GB | 1472257 | 5/1977 |
| WO | WO 97/46526 | 12/1997 |
| WO | WO 98/06403 | 2/1998 |
| WO | WO 98/40071 | 9/1998 |
| WO | WO 99/09981 | 3/1999 |

OTHER PUBLICATIONS

Chaiyabutr et al. "Urinary bladder effects after oral dosages of the antidiarrheal drug combination clioquinol-phanquinone-oxyhphenonium bromide in experimental dogs." Journal of the Medical Association of Thailand, 1985, vol. 68, No. 12, pp. 649-653.*

U.S. Appl. No. 09/485,909, filed Oct. 19, 2000, Xilinas and Gerolymatos.

* cited by examiner

Primary Examiner—Shengjun Wang
Assistant Examiner—Jennifer Kim
(74) Attorney, Agent, or Firm—Scully, Scott, Murphy & Presser, P.C.

(57) ABSTRACT

The use of phanquinone (4,7-phenanthroline-5,6-dione) for the treatment or prevention of memory impairment is suggested. Also a method for improving the learning or memory of a normal subject is suggested, said method comprising the administering of phanquinone, optionally together with one or more pharmaceutically acceptable carrier(s).

11 Claims, No Drawings

USE OF PHANQUINONE FOR THE TREATMENT OR PREVENTION OF MEMORY IMPAIRMENT

This is a continuation of U.S. application Ser. No. 09/895,807, filed Jun. 26, 2001, now abandoned, which is a continuation of International Application No. PCT/JB00/00011, filed Jan. 6, 2000, now abandoned, which claims priority to Greek Patent Application No. 990100005, filed Jan. 7, 1999, each of which is incorporated herein by reference in its entirety.

FIELD OF THE INVENTION

The present invention relates to the treatment or prevention of memory impairment and to a method of improving the learning and memory capabilities of normal subjects. Notably, the invention relates to the use of phanquinone for the prevention or treatment of memory impairment and to a method comprising the administering of phanquinone for improving the learning and the memory capabilities of a normal subject.

DESCRIPTION OF THE BACKGROUND ART

Memory is a complex mental function which includes the ability to learn, retain, and recall information. Memory impairment is often a symptom of dementia, amnesia, aphasia, senility, or age-associated cognitive deterioration. Dementia may be caused by i.a. Alzheimer's disease, Parkinson's disease, progressive supranuclear palsy, and amyotrophic lateral sclerosis.

Two types of memory are generally recognized, viz. short-term and long-term memory. The short-term memory is the ability to learn and briefly retain small amounts of information for a few seconds or minutes and to recall the information again. The long-term memory is the ability to learn and retain large amounts of information and recall those after long delays. Impairment of both types of memory may be symptoms of dementia.

The short-term memory is impaired for persons suffering from dementia in the early stages. Such persons have difficulty in learning new information and to retain it more than momentarily. As the disease progresses, new learning is severely curtailed and, gradually, the long-term memory is also lost.

Several compounds or mixtures of compounds have been suggested in the prior art for the treatment of mental decline.

Pyrrolidone or pyrrolidine derivatives for improving memory have been suggested in EP 239500, EP 165919, BE 892942, U.S. Pat. No. 5,102,882, EP 296978, EP 296979. Pyridine derivatives for the treatment of impairment of short-term memory are disclosed in U.S. Pat. No. 4,448,779. Choline derivatives for treating mental decline in the elderly is suggested in EP 201623. Indole or indolin derivatives for the improvement of processes involved in learning are disclosed in EP 241006, JP 6107544, U.S. Pat No. 5,494,928, WO 97/47598, and U.S. Pat. No. 4,778,812. Pilocardin derivatives for improving memory functions are disclosed in U.S. Pat. No. 4,977,176. Glycine-containing compositions for enhancing cognitive functions are disclosed in U.S. Pat. No. 5,731,349. Peptide derivatives for treating mental decline and improving mental capacity are disclosed in U.S. Pat. No. 5,439,930, RU 2099078, and WO 95/15310. Xanthine derivatives for the treatment of age-related memory impairment are disclosed in WO 94/19349.

Compounds enhancing the stimulus-induced release of neurotransmitters, especially acetylcholine, may also be used to treat memory impairment. Examples are 2-benzyl-2-propyl 2-amino-2-R-acetate derivatives disclosed in EP 293351, 1-(4-chlorophenyl)-2-methyl-2-propyl 2-amino-3-methyl-butanoate disclosed in GB 2205097, polycyclic hetero-aromatic derivatives disclosed in U.S. Pat. No. 5,300,642, 5-phenyl-4,4-dimethyl-3-oxo or hydroxy-pentylamine derivatives disclosed in EP 322391, 1-oxa-8-azaspiro(4.5) decane derivatives disclosed in EP 491562, derivatives of azacyclic and azabicyclic hydroxylamine disclosed in WO 94/00448, halogenated aromatic derivatives disclosed in EP 627400, derivatives of acyclic and cyclic amides disclosed in WO 95/29909, carbamoyloxypropylamine or carbamoyloxyethylamine derivatives disclosed in WO 96/08468.

Compounds that modulate the function of the kainate receptor may be used for improving memory. An example is alkyl carboxy amino acids, such as (2S,4R)-4-methyl glutamic acid, disclosed in WO 96/25387.

In EP 326381 it is suggested to use hypothalamic hypophysiotropic hormones, such as somatostatin and growth-hormone releasing factor, to improve the learning abilities.

DE 2555010 discloses the use of uronic acids for improving the cerebral efficiency in general, such as improvement of memory.

U.S. Pat. No. 4,481,206 discloses the improvement of memory when administering spiro(N'-methyl-4'-piperidyl)-N-ethyl-succinimide. This compound is a parasympathicomimetic substance also having cholinomimetic, analgetic and sedative activity.

WO 98/33498 discloses the use of breflate or analogous compounds thereof for the treatment of a mammal suffering from a cognitive dysfunction. Breflate or analogous compounds thereof enhance the long-term potential of nerve cells.

Phanquinone (4,7-phenanthroline-5,6-dione) has hitherto been used for the treatment of various disorders, such as amoebiasis. However, the treatment or prevention of memory impairment has not been suggested previously. Phanquinone has been marketed by CIBA-GEIGY as ENTOBEX®.

It is the object of the invention to provide a new use of a known pharmaceutical compound for the treatment or prevention of memory impairment. Another object of the invention is to provide a method of treating a subject suffering from or suspected of suffering from memory impairment. A further object of the invention is to provide a method for improving the learning and memory ability of a normal subject.

DISCLOSURE OF THE INVENTION

According to the present invention the use of phanquinone for the manufacture of a pharmaceutical composition for the treatment or prevention of memory impairment is provided.

Phanquinone may be administered in any amount efficient for the treatment or prevention of memory impairment. Preferably, phanquinone is administered in an amount of 5 mg to 250 mg, and most preferred 10 mg to 50 mg, one to three times daily. The pharmaceutical composition may be formulated for oral, parenteral or intradermal administration.

According to the present invention also a method for improving the learning or memory of a normal subject is provided, said method comprising the administering of phanquinone, optionally together with one or more pharmaceutically acceptable carrier(s). Phanquinone may be administered in any amount effective to improve the learning or the memory.

The invention also relates to a method of treating a subject suffering from or suspected of suffering from memory impairment, said method comprising administering to the subject an amount of phanquinone effective to treat or prevent the memory impairment.

According to the present invention also a method of treating a subject suffering from or suspected of suffering from memory impairment is provided, said method comprising administering to the subject an amount of phanquinone effective to improve learning or memory.

Phanqionone possesses a long-term as well as a short-term effect on the memory.

The short-term effect implies that the ability to retain and recall information from the memory is improved compared to the normal state, when phanquinone is administered immediately prior to a trial.

The long-term effect implies that the memory improving effect of phanquinone still is obtained several days after the administration has ceased.

The exact function of phanquinone in the body is not known yet. However, as the effect of phanquinone is pronounced in all parts of memory formation, including learning, retaining and recalling information, the effect of phanqionone is considered to be unspecific. Most likely, the effect of phanquinone is referred to enhanced arousal. This hypothesis is supported by the fact, that a general enhancement of activity is observed.

The above attempt to explain the observed effects of phanquinone is without prejudice to the scope of protection sought and must not be construed as limiting the invention to a specific mode of action.

DETAILED DESCRIPTION OF THE INVENTION

Phanquinone is preferably administered together with one or more pharmaceutical acceptable carrier(s). The carrier(s) must be "acceptable" in the sense of being compatible with the other ingredients of the composition and not deleterious to the recipients thereof. In a preferred embodiment, the phanquinone and optional further active constituents in a pharmaceutical composition are purified.

It will be appreciated that the amount of phanquinone and optional further active constituents required for said treatment, improvement or prevention will vary according to the route of administration, the disorder to be treated, the condition, age, the case history of the subject, the galenic formulation of the pharmaceutical composition, etc.

In general, a suitable therapeutically effective amount of phanquinone in the pharmaceutical composition would be e.g. 5 to 250 mg, preferably 10 to 50 mg.

The actually administered amounts of phanquinone and optional further active constituents may be decided by a supervising physician. If the pharmaceutical composition in addition to phanquinone comprises further active constituents those may be included therein for administering in combination concurrently, or in different compositions for administering substantially simultaneously but separately, or sequentially.

Therapeutic formulations include formulations suitable for parenteral (including intramuscular and intravenous), oral, rectal or intradermal administration, although oral administration is the preferred route. Thus, the pharmaceutical composition may be formulated as tablets, pills, syrups, capsules, suppositories, formulations for transdermal application, powders, especially lyophilized powders for reconstitution with a carrier for intravenous administration, etc.

The term "carrier" refers to a diluent, adjuvant, excipient, or vehicle with which phanquinone is administered. The carriers in the pharmaceutical composition may comprise a binder, such as microcrystalline cellulose, polyvinylpyrrolidone (polyvidone or povidone), gum tragacanth, gelatine, starch, lactose or lactose monohydrate; a disintegrating agent, such as alginic acid, maize starch and the like; a lubricant or surfactant, such as magnesium stearate, or sodium lauryl sulphate; a glidant, such as colloidal silicon dioxide; a sweetening agent, such as sucrose or saccharin; and/or a flavouring agent, such as peppermint, methyl salicylate, or orange flavouring.

Therapeutic formulations suitable for oral administration, e.g. tablets and pills, may be obtained by compression or moulding, optionally with one or more accessory ingredients. Compressed tablets may be prepared by mixing the constituent(s), and compressing this mixture in a suitable apparatus into tablets having a suitable size. Prior to the mixing, the phanquinone may be mixed with a binder, a lubricant, an inert diluent and/or a disintegrating agent and further optionally present constituents may be mixed with a diluent, a lubricant and/or a surfactant.

In a preferred embodiment, free-flowing phanquinone powder is mixed with a binder, such as microcrystalline cellulose, and a surfactant, such as sodium lauryl sulphate, until a homogeneous mixture is obtained. Subsequently, another binder, such as polyvidone, is transferred to the mixture under stirring. Said mixture is passed through granulating sieves and dried by desiccation before compression into tablets in a standard compressing apparatus.

In a second preferred embodiment, free-flowing phanquinone powder is mixed with surfactants and/or emulsifying agents, such as Sapamine® (N-(4'-stearoyl amino phenyl)-trimethylammonium methyl sulphuric acid) and lactose monohydrate until a uniform distribution of the constituents is obtained. A second preparation containing a disintegrating agent, such as maize starch, is added to the phanquinone mixture under continuous stirring. Such a second preparation may be obtained by adding excess boiling water to maize starch suspended in cold water. The final mixture is granulated and dried as above and mixed with maize starch and magnesium stearate and finally compressed into tablets in a standard apparatus.

A tablet may be coated or uncoated. An uncoated tablet may be scored. A coated tablet may be coated with sugar, shellac, film or other enteric coating agents.

Therapeutical formulations suitable for parenteral administration include sterile solutions or suspensions of the active constituents. An aqueous or oily carrier may be used. Such pharmaceutical carriers may be sterile liquids, such as water and oils, including petroleum, animal, vegetable or synthetic origin, such as peanut oil, soy bean oil, mineral oil, sesame oil and the like. Formulations for parenteral administration also include a lyophilized powder comprising phanquinone and optionally further active constituents that is to be reconstituted by dissolving in a pharmaceutically acceptable carrier dissolving the active constituents, e.g. an aqueous solution of carboxymethylcellulose and lauryl sulphate.

When the pharmaceutical composition is a capsule, it may contain a liquid carrier, such as a fatty oil, e.g. cacao butter.

Suitable pharmaceutical excipients include starch, glucose, lactose, sucrose, gelatine, malt, rice, flour, chalk, silica gel, sodium stearate, glycerol monostearate, talc, sodium chloride, dried skim-milk, glycerol, propylene, glycol, water, ethanol and the like. Said compositions may form solutions, suspensions, emulsions, tablets, pills, capsules, powders, sustained-release formulations and the like. The composition can be formulated as a suppository, with traditional binders and carriers such as triglycerides.

In one embodiment of the pharmaceutical composition according to the invention, phanquinone and the possible further active constituents, are comprised as separate pharmaceutical entities. The two entities may administered simultaneously or sequentially.

Other features and advantages of the invention will be apparent for the skilled person.

EXAMPLE 1

Preparation of a Pharmaceutical Composition Comprising Phanquinone 250 g of phanquinone was mixed with 200 g sapamine® (N-(4'-stearoyl amino-phenyl)-trimethylammonium methyl sulphuric acid) and 1025 g lactose mono-hydrate for a period of 5 minutes. 300 g of boiling water was added at a time to a mixture of 100 g maize starch in 100 g cold water. The maize suspension, cooled to 40° C., was added to the phaniquinone-containing powder mixture under continuous stirring. The mixture was granulated using a 2.5 mm sieve and desiccated for 18 hours at 40° C. The dry granules were mixed with 400 g maize starch and 20 g magnesium stearate. The final mixture was formulated into tablets having a diameter of 8.0 mm and a weight of 200 mg.

What is claimed is:

1. A method of treating a subject suffering from memory impairment, comprising administering to the subject an amount of phanquinone effective to treat the memory impairment, provided that the memory impairment is not caused by Alzheimer's disease.

2. A method of treating a subject suffering from memory impairment, comprising administering to the subject an amount of phanquinone effective to improve learning or memory, provided that the memory impairment is not caused by Alzheimer's disease.

3. The method of claim 1, wherein the memory impairment is caused by Parkinson's disease.

4. The method of claim 2, wherein the memory impairment is caused by Parkinson's disease.

5. The method according to claim 1, 2, 3 or 4 wherein the amount of phanquinone is 5 mg to 250 mg.

6. The method according to claim 1, 2, 3 or 4, wherein the amount of phanquinone is 10 mg to 50 mg.

7. The method of according to claim 1, 2, 3 or 4, wherein the subject is human.

8. The method according to claim 1, 2, 3 or 4, wherein phanquinone is administered for up to ten years.

9. The method according to claim 1, 2, 3 or 4 wherein phanquinone is administered orally.

10. The method according to claim 1, 2, 3 or 4, wherein phanquinone is administered parenterally.

11. The method according to claim 1, 2, 3 or 4 wherein phanquinone is administered intradermally.

* * * * *